(12) United States Patent
Malawer

(10) Patent No.: US 8,110,002 B2
(45) Date of Patent: Feb. 7, 2012

(54) AMPUTATION BONE CAP

(76) Inventor: Martin M. Malawer, McLean, VA (US)

( * ) Notice: Subject to any disclaimer, the term of this patent is extended or adjusted under 35 U.S.C. 154(b) by 305 days.

(21) Appl. No.: 12/356,755

(22) Filed: Jan. 21, 2009

(65) Prior Publication Data

US 2010/0016992 A1 Jan. 21, 2010

Related U.S. Application Data

(60) Provisional application No. 61/006,507, filed on Jan. 17, 2008.

(51) Int. Cl.
*A61F 2/28* (2006.01)
(52) U.S. Cl. .................................. 623/16.11; 623/23.44
(58) Field of Classification Search .................... None
See application file for complete search history.

(56) References Cited

U.S. PATENT DOCUMENTS

| | | | |
|---|---|---|---|
| 4,007,494 A | 2/1977 | Sauer | |
| 4,092,741 A | 6/1978 | David | |
| 4,158,895 A | 6/1979 | Frosch et al. | |
| 4,547,912 A | 10/1985 | Sherva-Parker | |
| 5,352,227 A | 10/1994 | O'Hara | |
| 5,397,360 A | 3/1995 | Cohen | |
| 5,505,735 A | 4/1996 | Li | |
| 5,645,589 A | 7/1997 | Li | |
| 6,197,065 B1 * | 3/2001 | Martin et al. | 623/23.17 |
| 6,302,913 B1 | 10/2001 | Ripamonti et al. | |
| 6,843,808 B2 | 1/2005 | Grundei | |
| 6,969,406 B2 | 11/2005 | Tornier | |
| 2006/0129247 A1 | 6/2006 | Brown et al. | |
| 2007/0055255 A1 | 3/2007 | Siegel | |
| 2007/0150070 A1 | 6/2007 | Kim et al. | |

FOREIGN PATENT DOCUMENTS

DE 4338746 A1 * 5/1995
WO 2007013948 A2 2/2007

* cited by examiner

*Primary Examiner* — Thomas J Sweet
*Assistant Examiner* — Brian Dukert
(74) *Attorney, Agent, or Firm* — Studebaker & Brackett PC; Donald R. Studebaker

(57) ABSTRACT

A muscle fastening cap includes a head having one or more groups of openings along a direction of its axial length. The cap also may include a stem adapted for insertion into a muscle-supporting structure such as an intramedullary canal or a prosthesis device.

20 Claims, 5 Drawing Sheets

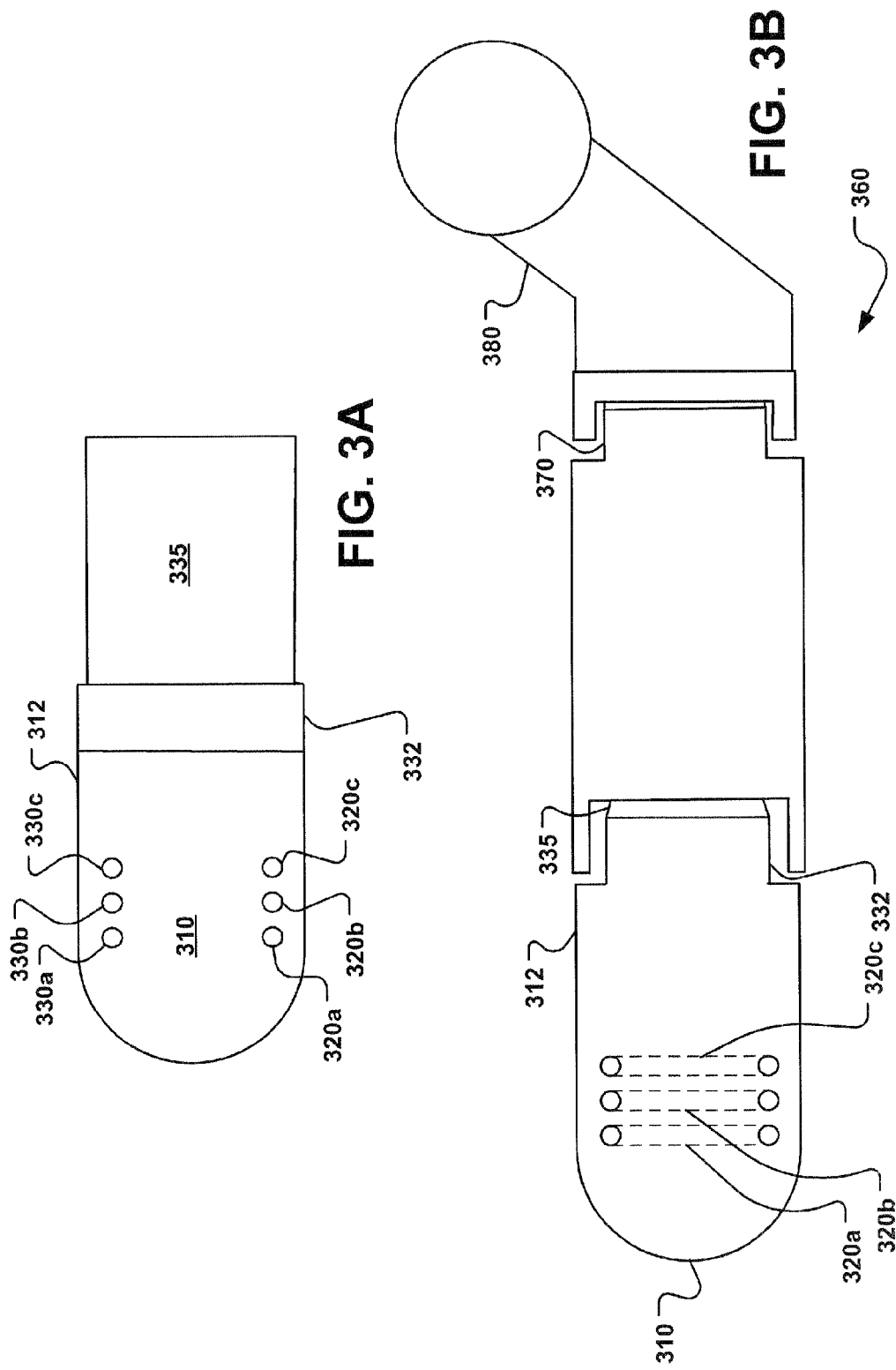

AMPUTATION BONE CAP

CROSS REFERENCE TO RELATED APPLICATIONS

The present application claims priority to U.S. Provisional Application No. 61/006,507 filed Jan. 17, 2008, the entire contents of this application being incorporated herein by reference in its entirety.

FIELD OF THE INVENTION

The invention relates to a fastening cap for attaching muscles, and more particularly to a cap for terminating a bone or prosthesis device and fastening muscles and as a device to close off the intramedullary canal of a bone following amputation and/or to extend the length of the remaining bone stump

BACKGROUND

General, vascular and plastic surgeons perform between 185,000 to 200,000 amputations each year in the United States on patients of all ages, including military personnel, as well as civilian children, adults, and the elderly. Several apparatuses and techniques are used by surgeons to control pain and prevent post-operative bleeding associated with these procedures and to enable the implementation of prosthetic fittings. For example, a bone cap can be used to cover the exposed end of an excised bone to limit bone overgrowth that can potentially lead to friction and pressure on the surrounding muscle and limb. There is no device to date, that can provide the attachment and balancing of the adjacent transected muscles to attach to the bone stump inorder to adjust and to balance the muscle tension of the remaining muscles to avoid the well known problem of stump contractures which often occurs following amputation of various bones at different anatomic levels of amputation.

SUMMARY

In one aspect of the invention, a muscle fastening cap includes a head including a first portion having one or more groups of openings for attaching muscle tissue along a direction of its axial length. The head also includes a second portion for providing a stem that connects to a muscle-supporting structure. The muscle fastening cap also includes a stem extending from the second portion of the head. The stem is adapted for insertion into a muscle-supporting structure. The head is configured to be exposed in relation to a muscle-supporting structure to allow attaching at least one surgical tape to the first portion for fastening said muscle tissue.

In another aspect of the invention, a modular muscle-fastening system includes a first head portion and a stem portion which extends from the first portion. The first portion includes at least one group of holes substantially aligned along a first direction. The stem portion is configured to mate with a member of a prosthesis device to provide a mechanical connection between the stem portion and the prosthesis device. Each through hole is configured to receive at least one surgical tape for fastening muscle tissue to the first head portion, and the head portion is configured to be exposed in relation to the member of the prosthesis device to allow attaching the at least one surgical tape to the head portion for fastening said muscle tissue.

In yet another aspect of this invention, a method of fastening a modular muscle of an amputee includes providing a muscle cap having a first portion and a second portion, the first portion includes at least one group of through holes substantially aligned along a first direction and the second portion forming a stem extending from the first portion in the first direction. The stem portion is positioned in the muscle-supporting structure and a plurality of surgical tapes is passed through the respective through holes formed in the first portion. The surgical tapes are then secured to adjacent muscle tissue.

Additional aspects and advantages of the invention will be set forth in the description that follows, and in part will be apparent from the description, or may be learned from practice of the invention. The aspects and advantages of the invention will be realized and attained by the system and method particularly pointed out in the written description and claims hereof as well as the appended drawings.

It is to be understood that both the foregoing general description and the following detailed description are exemplary and exemplary only and are not restrictive of the invention, as claimed.

BRIEF DESCRIPTION OF THE DRAWINGS

The accompanying drawings, which are included to provide a further understanding and are incorporated in and constitute a part of this specification, illustrate embodiments of the invention that together with the description serve to explain the principles of the invention. In the drawings:

FIG. 3A is a diagram of an exemplary muscle fastening cap for use in modular assemblies.

FIG. 3B is a diagram of an exemplary muscle fastening cap coupled to a prosthetic according to an exemplary modular assembly.

DETAILED DESCRIPTION

Figure 1:
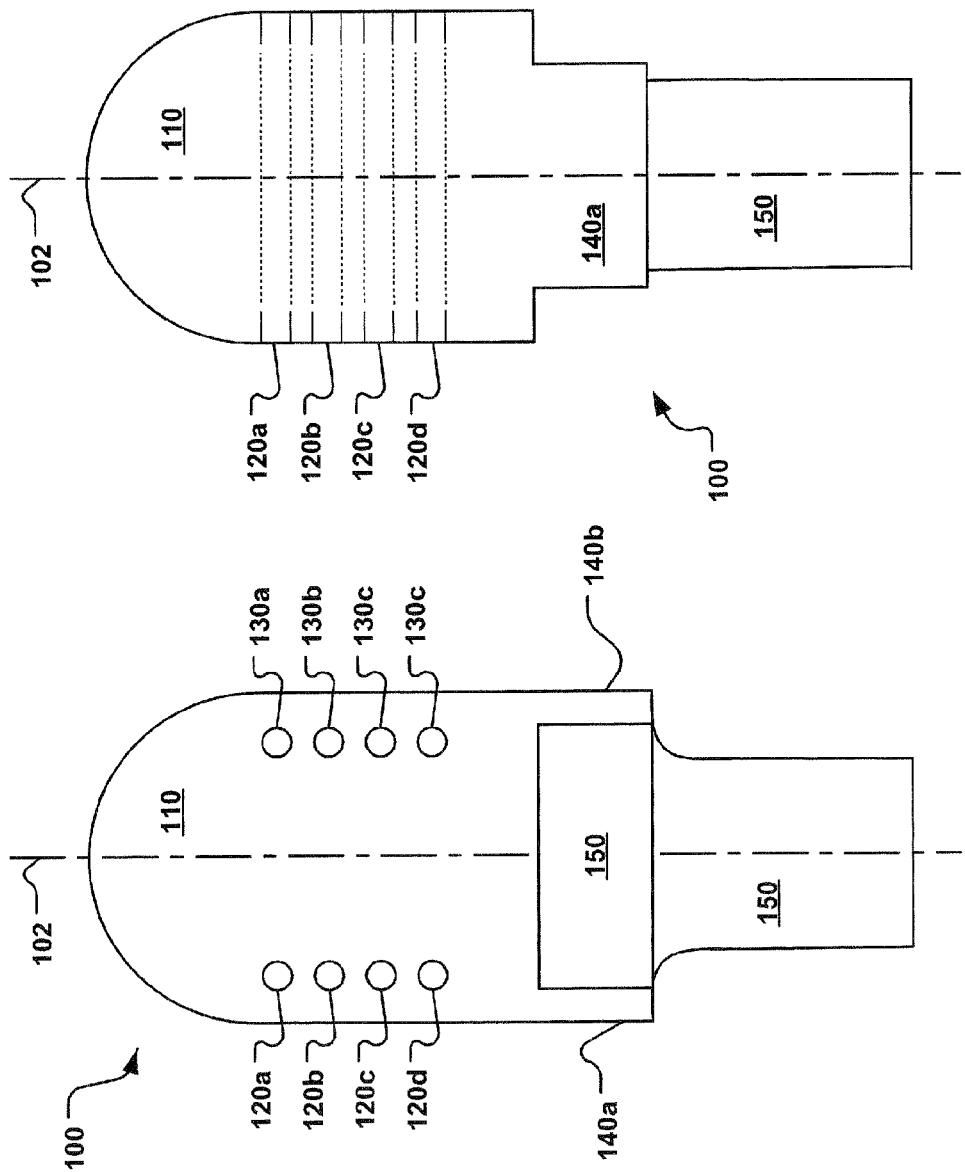
FIGS. 1A and 1B are diagrams respectively showing front and side views of an exemplary muscle fastening cap according to some embodiments.

FIGS. 1A and 1B respectively show a front and side view of an exemplary fastening cap 100 according to some embodiments attachable to a muscle-supporting structure, such as a bone or a prosthesis device. The fastening cap 100 may be made from any biocompatible material, such as cobalt chrome or titanium, although other biocompatible metal alloys, composites or materials may be used. With reference first to FIG. 1A, a fastening cap 100 includes a rounded head 110 and openings 120a to 120d, and 130a to 130d on opposing sides of the head 110 and along the direction of axis 102. The head 510 may be of a varying length and a varying diameter. The head 510 may also be of varying shape, such as hemispherical or conical, for example. While FIG. 1 shows four openings along two sides of the fastening cap 100, more or fewer holes may be included on the head 110 along a greater or smaller number of sides.

As shown in FIG. 1A, the fastening cap 100 may be provided with two skirt portions 140a and 140b that extend further than the rest of the head and are arranged to receive a stem 150, which may be adapted for attachment to a muscle-supporting structure, such as a canal of a hollowed out bone or to a prosthesis device, for example. FIG. 1B shows the fastening cap 100 of FIG. 1A rotated 90 degrees to show that the openings 120a to 120d and 130a to 130d can extend through the head 110, although only the openings 120a to 120d and one skirt portion 140a are shown for clarity of illustration. The head 110 can be attached to the stem 150 by any of a variety of known ways. For example, the head 110 and stem 150 can be fit together with a taper, such as a Morse taper although other methods of mechanically connecting the head to the stem can be used. For instance, the head 110 can be inserted into the stem 150 and twisted into place. In other embodiments, the head and stem can comprise a single part.

Figure 2:
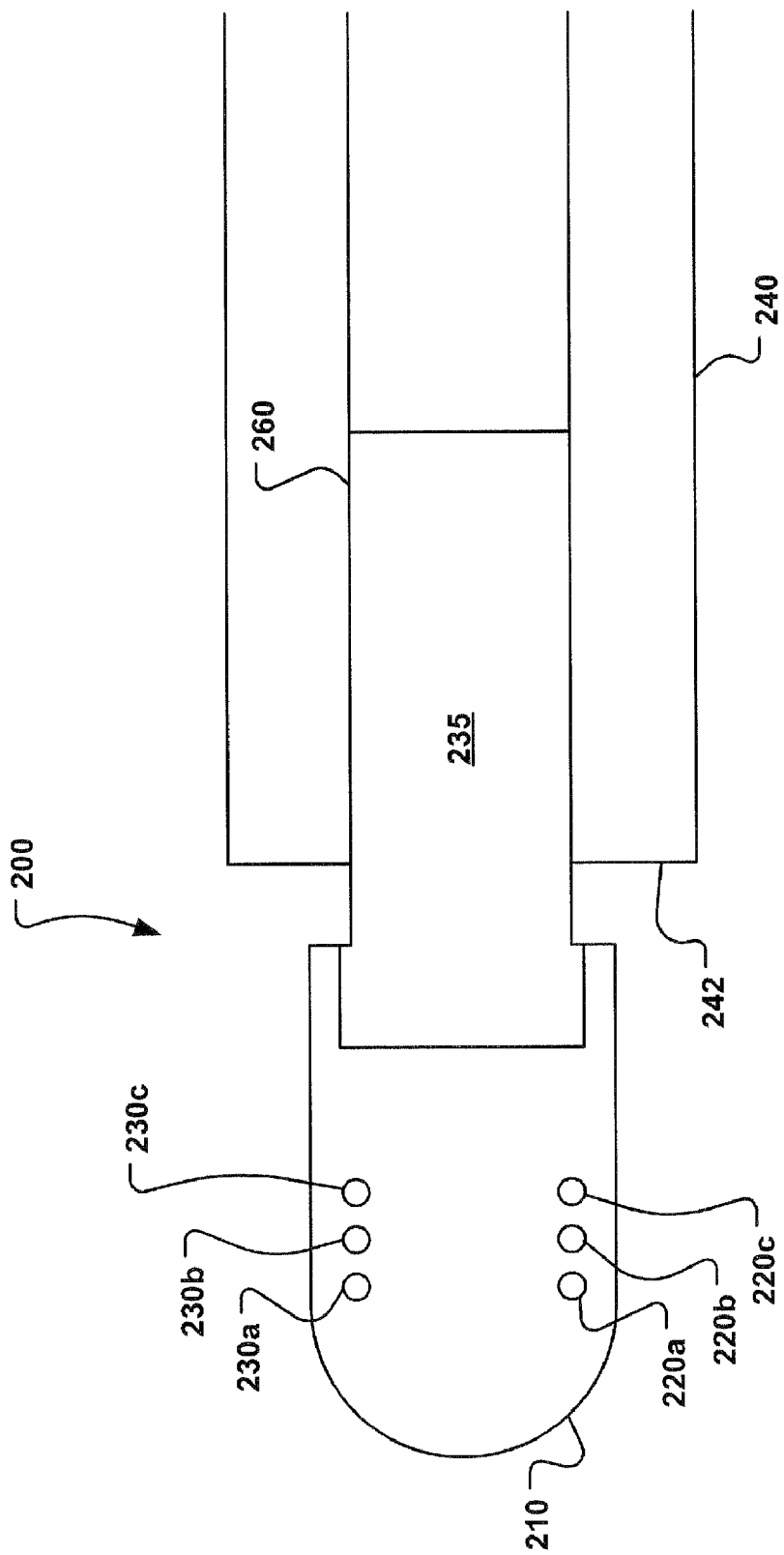
FIG. 2 is a diagram of an exemplary muscle fastening cap coupled to a bone canal.

FIG. 2 shows an exemplary embodiment of a muscle fastening cap 200 including a head 210 and openings 220a to 220c, and 230a to 230c. The head 210 is connected to a stem 235 that can be inserted into an intramedullary canal 260 of a partially hollowed out bone 240. For example, marrow from the intramedullary canal of a bone can be removed from the excised end 242 of the bone 240. The stem 235 can be fixed in place in the bone canal 260 by impaction, or by a biocompatible adhesive such as polymethylmethacrylate (PMMA). The stem 235 can be of a varying length and a varying diameter, depending on the kind of bone and the size of intramedullary canal 260 into which the stem 235 is being inserted. For example, a stem of a muscle fastening cap to be inserted into a femur may have a longer length and larger diameter than a stem of a muscle fastening cap to be inserted into a humerus.

FIG. 3A depicts a muscle fastening cap according to some embodiments, that includes a first portion 310, a group of through holes 320a to 320c and a group of through holes 330a to 330c aligned in the direction of elongation of the first portion 310. A second portion 312 joins a central portion 332, which in turn joins a stem portion 335.

Figure 4A:
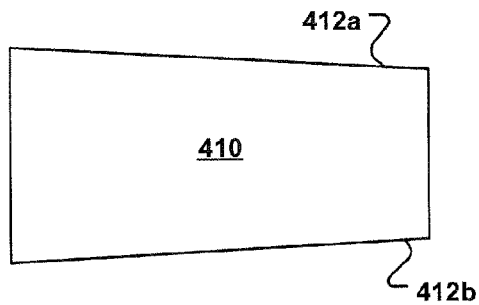
FIGS. 4A, 4B, 4C, and 4D are diagrams of various types of stems that can be inserted into a bone canal.
Figure 4B:
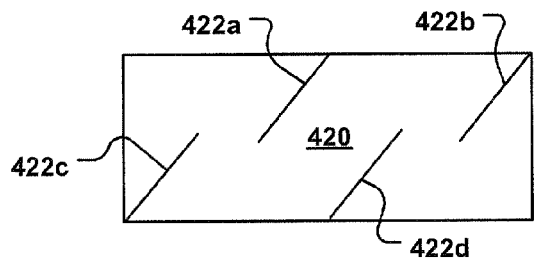
Figure 4C:
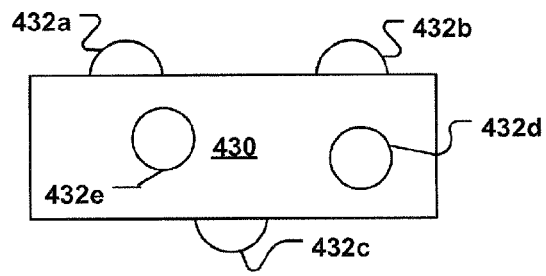
Figure 4D:
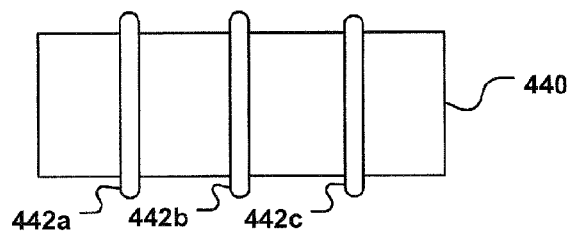

The stem 335 can be a variety of shapes and sizes and can have a variety of surfaces to join to a muscle-supporting structure such as a bone canal or a modular prosthesis. For example, FIG. 4A shows a stem 410 featuring a tapered end where sides 412a and 412b approach one another at one end to enable a taper connection with another prosthesis piece (e.g., a Morse taper fit). The tapered end can also provide a friction fit into the intramedullary canal. A stem can also have a rough or textured surface or fluted edges to better engage the muscle fastening cap to a bone or bone-like structure. For example, FIG. 4B is a diagram of a stem 420 featuring threads 422a to 422d which can urge the stem more securely into an intramedullary canal and/or fasten the stem to another modular-type prosthesis piece. FIG. 4C shows bumps or protrusions 432a to 432e on the surface of a stem 430 and FIG. 4D shows a series of ridges or ribs 442a to 442c along a stem 440. Although not shown, the stem can also comprise a flange with sharpened edges. Such anchoring mechanisms may be included individually or in any combination to promote better integration of a stem with an intramedullary canal or to a modular prosthesis piece, or another kind of fitting may be used.

Figure 5:
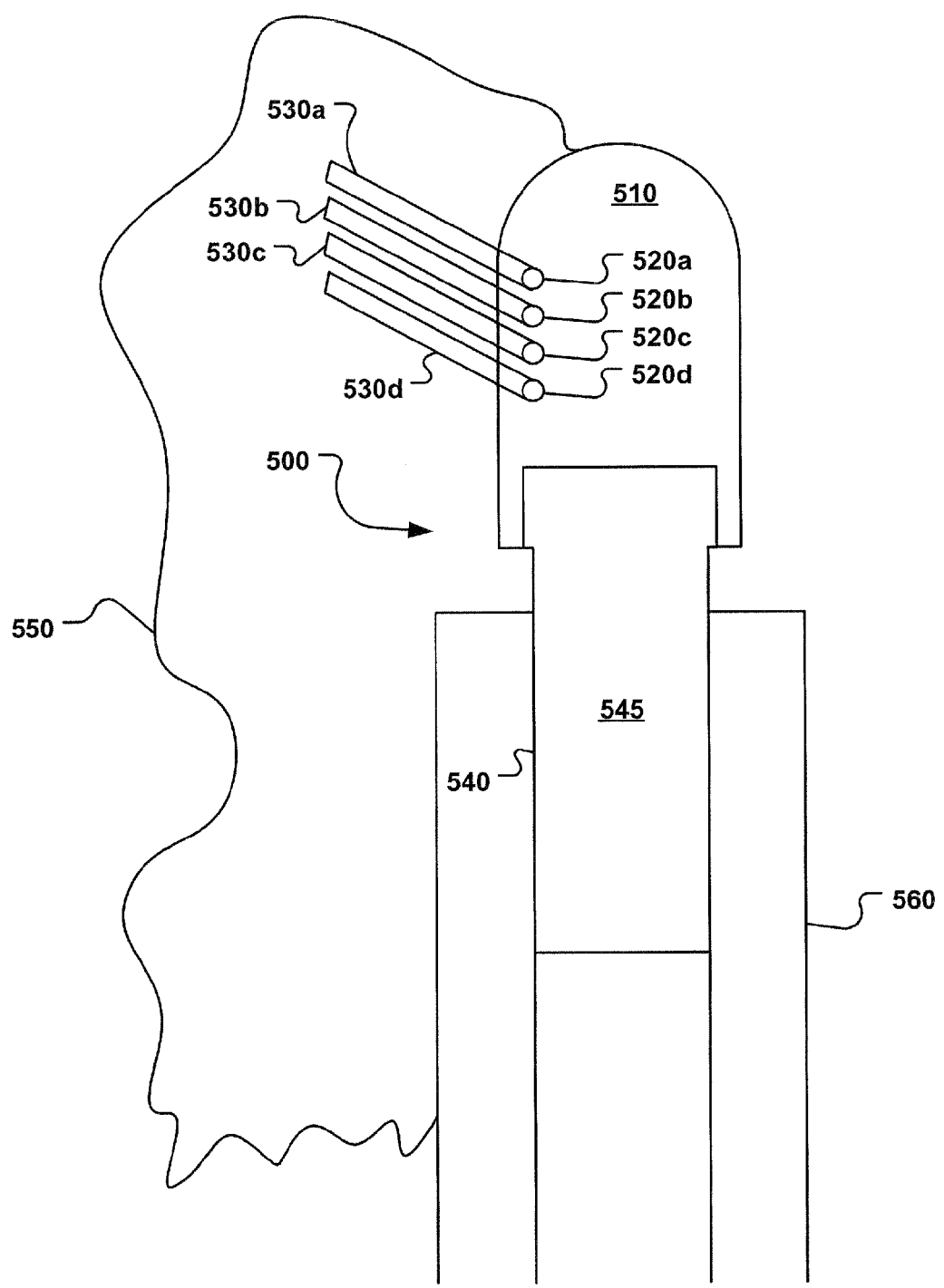
FIG. 5 is a diagram showing an exemplary muscle fastening cap attached to a muscle.

The cap and stem of FIG. 3A may be a unit within a system of orthopedic modularity. Referring now to FIG. 3B, a muscle fastening cap such as the one shown in FIG. 3A is a unit of a modular system which can include a modular prosthesis 360. The muscle fastening cap with the first portion 310, the group of through holes 320a to 320c, the second portion 312, and the central portion 332 can be inserted into the modular prosthesis 360 via connection with the stem portion 335. For example, the connection between the stem portion 335 and the modular prosthesis 360 can be provided with a taper fit. This can provide a multi-joint prosthesis, including a tapered stem that can prevent sliding movement of the prosthesis into the intramedullary passageway of a bone. While a multi-joint modular prosthesis 360 including a connection point 370 and a ball module 380 is shown in FIG. 3B, a modular prosthesis can include only a single piece or be a highly complex prosthetic device. The prosthesis may be an internal prosthesis, for example, an artificial hip joint or other kind of artificial joint. Additionally, the prosthesis may also be an external prosthesis, providing an artificial leg or other kind of artificial limb FIG. 5 shows a muscle fastening cap 500, having a head 510 and a group of openings 520a to 520d. The cap 500 is inserted into an intramedullary canal 540 of a partially hollowed out bone 560 via a stem portion 545. A muscle 550 that surrounds the bone 560 may be anchored to the head 510 by passing surgical tapes 530a to 530d through the muscle 550 located around the bone 560 and through the openings 520a to 520d provided in the head 510. This tape could be, for example, Dacron tape or another kind of biocompatible suture. The tension in the tapes 530a to 530d can be adjusted to provide a suitable attachment of the muscle 550 to the head 510. The surgical tapes can then be secured with a surgical knot to anchor the muscle 550 to the head 510.

The bone 560 can be, for example, the distal end of a residual limb. A residual limb can be created through a disarticulation across one of the following: the humerus (above the elbow), the radius (below the elbow), the femur (above the knee), or the tibia (below the knee) and an exemplary fastening cap could be used in any of the related residual limbs. The tapes can be attached to the holes in the head 510 as well as the major muscle groups of the limb. For example, adductors, the hamstrings, and the quadriceps of the thigh can be attached to the head 510 of the muscle fastening cap for an above the knee amputation. However, there could be a greater or smaller number of muscles attached to the muscle-supporting structure.

Attachment of the muscles to a muscle fastening cap via surgical tapes, as described in embodiments herein, can prevent contractures (i.e., irreversible muscle contraction or shortening that occur over time as a result of unnatural stress on the limb). Additionally, by stabilizing the tissue surrounding the distal limb, bursas can be prevented from developing at an amputation tip, which reduces pain and discomfort. A muscle fastening cap, as described herein, also can also provide a cap for overgrowth of an excised bone, for example a cap for bone overgrowth in amputations performed on children and adolescents. Therefore, implementing a muscle fastening cap described herein can provide ways to decrease pain, and retain flexibility and mobility for amputees of all ages.

U.S. Pat. No. 7,374,577 describes an implant device including a plate that is adapted for insertion into an intramedullary canal and has a plurality of muscle fixing holes dispersed on the plate. While these muscle fixing holes can be used to secure the muscle, the length and diameter of the plate is generally fixed to that required to adequately cap the bone. More particularly, this device is applied to a leg amputation, as a load bearing device to improve ease of walking with a leg prosthesis. By contrast, the muscle fastening cap described herein can be incorporated in a variety of limbs. The muscle fastening cap described herein can also vary in length to increase the overall length of an excised bone, permitting improved fitting, greater comfort, and mobility for a prosthesis device. This is especially useful for younger patients with smaller limbs or other patients with shorter distal limbs that would benefit from being lengthened.

The muscle fastening cap can be conveniently used by general, vascular and plastic surgeons as well as orthopedic surgeons because it would require little or no instrumentation to enable insertion, and can be easily and conveniently stored as individual parts that can be fit together as required. This muscle fastening cap provides an improvement over the previous method of suturing distal muscles directly to the residual bone, which can weaken the bone and provide unreliable connection points with the muscle groups. Further, because the muscle fastening cap is inserted into the intramedullary canal, pain and postoperative bleeding that result from an excised limb can be reduced or prevented by capping the excised bone. The muscle fastening cap can prevent bleeding by functioning as a cork within the bone. The cap can also reduce post-operative pain as well as phantom pain syndromes by closing the open canal, similar to the pain relief provided by a filling in a tooth cavity.

It will be apparent to those skilled in the art that various changes and modifications can be made in the method and system for accumulating and presenting device capability information of the present invention without departing from the spirit and scope thereof. Thus, it is intended that the invention cover the modifications of this invention provided they come within the scope of the appended claims and their equivalents.

What is claimed is:

1. A muscle fastening cap, comprising:
    a head including a first portion, said first portion comprising at least one group of openings for attaching muscle tissue provided along a direction of an axial length of the head;
    a second portion configured to provide a stem along said direction of the axial length of said head, said stem configured to connect to a muscle-supporting structure; and
    a stem, said stem extending from the second portion of the head and adapted for insertion into a muscle-supporting structure, wherein
    said head is configured to be exposed in relation to a muscle-supporting structure to allow attaching at least one surgical tape to said first portion for fastening said muscle tissue.

2. The cap of claim 1, wherein the head and the stem comprise one integral part.

3. The cap of claim 1, wherein the head and the stem comprise two parts.

4. The cap of claim 1, wherein the openings extend through the head in a direction substantially perpendicular to the direction of the axial length.

5. The cap of claim 1, wherein the head has a hemispherical shape.

6. The cap of claim 1, wherein the head has a conical shape.

7. The cap of claim 1, wherein the stem is capable of being anchored to a bone canal by impaction.

8. The cap of claim 1 being composed of cobalt chrome or titanium.

9. The cap of claim 1, wherein the muscle-supporting structure is a bone.

10. The cap of claim 1, wherein the muscle-supporting structure is a prosthesis device.

11. The cap of claim 1, wherein the head is substantially rounded at the first portion.

12. The cap of claim 1, wherein a first group of the openings is arranged along one side of the head, and a second group of the openings is arranged along another side of the head opposite the first group.

13. The cap of claim 1, wherein the stem comprises a flange.

14. A modular muscle fastening system, comprising:
    a first head portion including at least one group of through holes substantially aligned along a first direction; and
    a stem portion extending from the first portion in the first direction,
    wherein the stem portion is configured to mate with a member of a prosthesis device to provide a mechanical connection between the stem portion and the prosthesis device, each through hole is configured to receive at least one surgical tape for attaching muscle tissue to the first head portion, and said head portion is configured to be exposed in relation to the member of the prosthesis device to allow attaching said at least one surgical tape to said head portion for attaching said muscle tissue.

15. The system of claim 14, wherein the stem portion comprises a tapered surface.

16. The system of claim 14, wherein the first head portion and stem portion are formed of a single integral material.

17. The system of claim 14, wherein the first head portion has a hemispherical shape.

18. The system of claim 14, wherein the first head portion has a conical shape.

19. The system of claim 14, wherein the stem portion can be a female part.

20. The system of claim 14, wherein the member of a prosthesis device can be a female part.

* * * * *